United States Patent [19]

Takemura et al.

[11] Patent Number: 5,202,334
[45] Date of Patent: Apr. 13, 1993

[54] PYRAZOLO(1,5-A)PYRIDINE COMPOUNDS, AND PRODUCTION AND USE THEREOF

[75] Inventors: Shoji Takemura, Yao; Yasuyoshi Miki, Osaka; Jun Yamada, Takarazuka; Kunihiro Miyazeki, Takatsuki, all of Japan

[73] Assignee: Senju Pharmaceutical Co., Ltd., Osaka, Japan

[21] Appl. No.: 729,352

[22] Filed: Jul. 12, 1991

[30] Foreign Application Priority Data

Jul. 18, 1990 [JP] Japan .................................. 2-191075
Jan. 21, 1991 [JP] Japan .................................. 3-82058

[51] Int. Cl.$^5$ .................... A61K 31/435; C07D 471/04
[52] U.S. Cl. .................................. 514/300; 546/121
[58] Field of Search .......................... 546/121; 514/300

[56] References Cited

U.S. PATENT DOCUMENTS 3,850,941 11/1974 Irikura et al. ...................... 546/121

Primary Examiner—Bernard Dentz
Attorney, Agent, or Firm—Burgess, Ryan & Wayne

[57] ABSTRACT

A novel anti-serotonergic compound and the synthetic intermediates thereof are provided.

The compound and intermediates are pyrazolo[1,5-a]pyridine compounds represented by the formula,

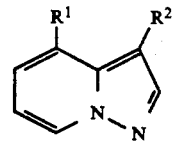

wherein $R^1$ represents —OH, —OCH$_2$-Ph (where Ph is a phenyl group),

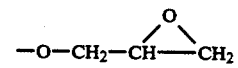

or —O—CH$_2$—CH(OH)—CH$_2$—NH—CH(CH$_3$)$_2$; and $R^2$ is H or —COOR (wherein R is a C$_1$-C$_3$ alkyl group). Among the compounds of the above formula, a compound wherein $R^1$ is —O—CH$_2$—CH(OH)—CH$_2$—NH—CH(CH$_3$)$_2$ has anti-serotonergic activity and can be synthesized, for example, by way of compounds wherein $R^1$ is OCH$_2$Ph and $R^2$ is COOR, $R^1$ is —OH and $R^2$ is H, and $R^1$ is

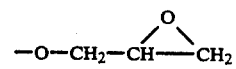

and $R^2$ is H, in order.

8 Claims, 1 Drawing Sheet

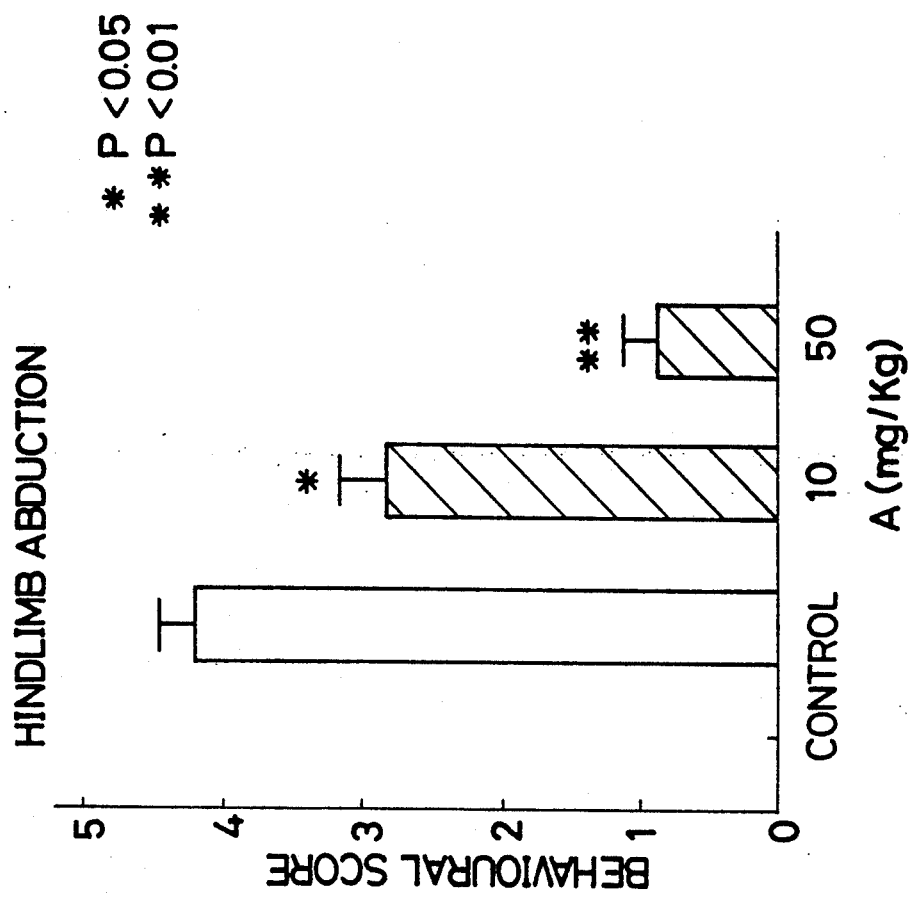
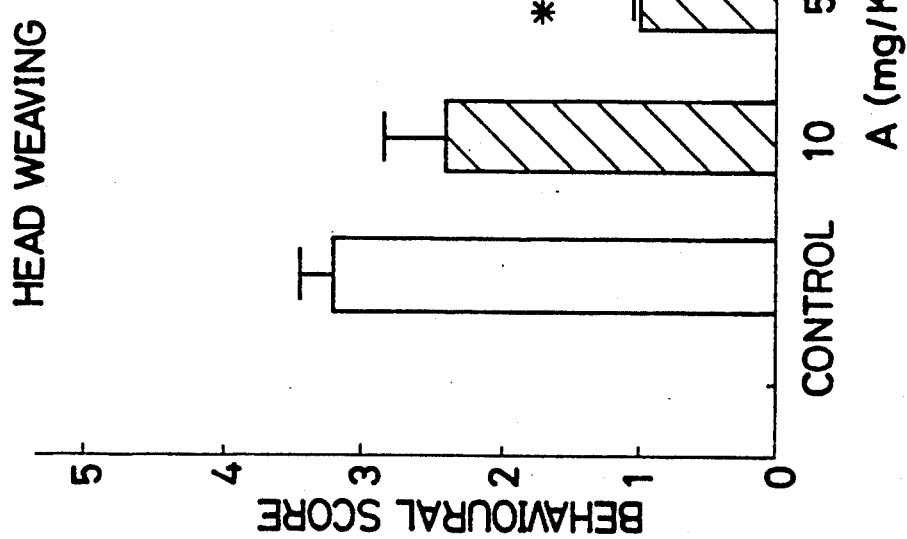

PYRAZOLO(1,5-A)PYRIDINE COMPOUNDS, AND PRODUCTION AND USE THEREOF

BACKGROUND OF THE INVENTION

1) Field of the Invention

This invention relates to 1-(isopropylamino)-3-(pyrazolo[1,5—a]pyrid-4-yloxy)-2-propanol which exhibits anti-serotonergic activity, and to a production process and use thereof.

2) Background Art

As the antiserotonin-acting substance, there are known the compounds as represented by the following formulae:

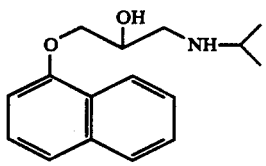
Propranolol

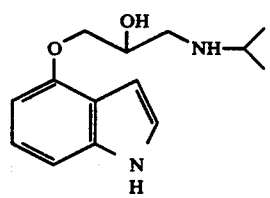
Pindolol

These compounds have a naphthalene or indole ring as their basic skeletons, but a compound, which is more easily degradable and shows a shortened half-life in the body, is desired.

SUMMARY OF THE INVENTION

The present inventors have succeeded in the production of 1-(isopropylamino)-3-(pyrazolo[1,5—a]pyrid-4-yloxy)-2-propanol [the following formula (A)] which is a novel compound having a pyrazolopyridine ring as the basic skeleton,

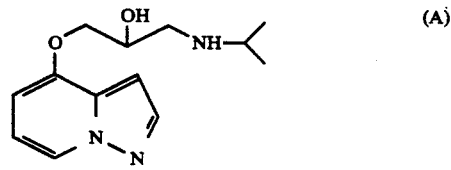

The Compound (A) possesses anti-serotonergic activity and can be produced through the following synthetic pathways:

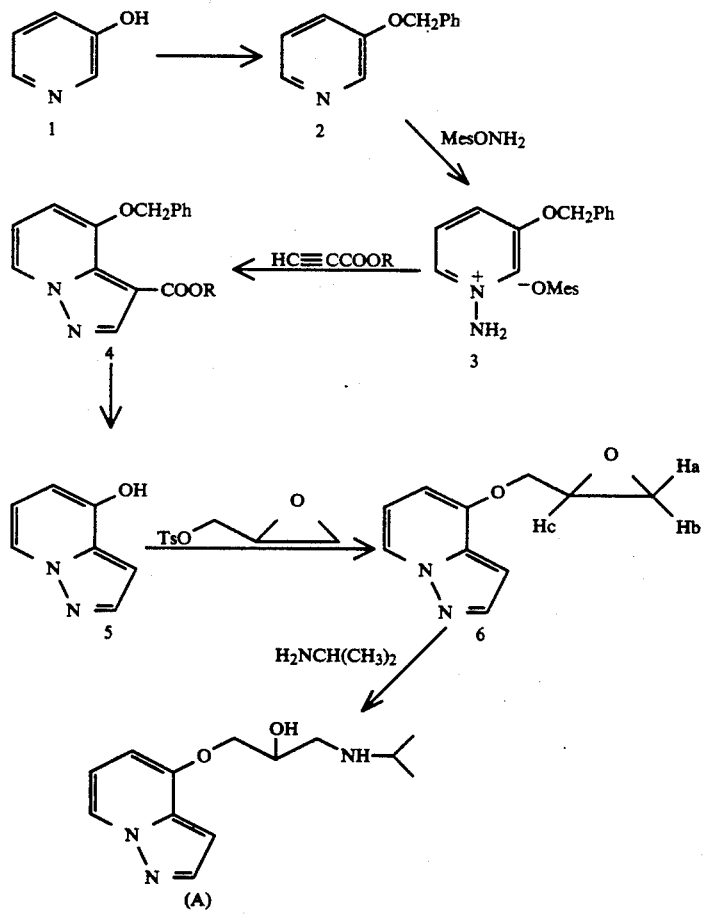

[wherein Ph represents a phenyl group; Mes represents a mesitylenesulfonic acid group; R represents a $C_1$–$C_3$ lower alkyl group; and Ts represents a tosyl group].

DESCRIPTION OF THE PREFERRED EMBODIMENTS

In the above reaction scheme, the Compounds (2), (3), (4), (5), (6) and (A) are novel, and among them, the compounds having the pyrazolopyridine skeleton are represented by the general formula as given below:

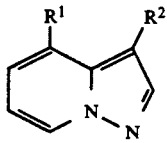

[wherein $R^1$ represents —OH, —OCH$_2$Ph (where Ph is a phenyl group),

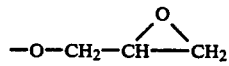

or —O—CH$_2$—CH(OH)—CH$_2$—NH—CH(CH$_3$)$_2$; and $R^2$ represents H or —COOR (where R is a $C_1$-$C_3$ alkyl group)].

The above-mentioned synthetic pathways are explained in the following:

In the first place, 3-hydroxypyridine (1) is benzylated for the purpose of protecting the hydroxyl group, producing 3-benzyloxypyridine (2). This reaction can be carried out, for example, by allowing benzyl chloride to act on the Compound (1) in the presence of a deacidifying agent, such as sodium hydroxide.

Then, the compound (2) is reacted with O-mesitylenesulfonylhydroxylamine to give N-amino-3-benzyloxypyridinium mesitylenesulfonate (3). The reaction can be allowed to proceed in such a solvent as methylene chloride, under ice-cooling, if desired.

The resulting Compound (3), after action of such a base as anhydrous potassium carbonate, is treated with a lower alkyl ester of propiolic acid, whereupon a cyclization reaction takes place to yield 4-benzyloxypyrazolo[1,5—a]-pyridine-3-carboxylic acid lower alkyl ester (4). This reaction can be allowed to proceed in such a solvent as dimethylformamide at room temperature. The production of the Compound (4) is generally accompanied by the formation of the 6-benzyloxy derivative which is the isomer of the Compound (4), and the two compounds each can be separated from the other by suitable means, such as column chromatography.

In the next place, the Compound (4) is subjected to removal of its benzyl and alkoxycarbonyl groups to give 4-hydroxypyrazolo[1,5-a]pyridine (5).

The removal reaction may be conducted in stepwise; firstly, the alkoxycarbonyl group is hydrolyzed in the presence of an alkali such as alkali hydroxide to convert to the carboxyl group, and then heated in a solvent under the addition of copper chromite (2CuOCr$_2$O$_3$) or reacted with a strong acid such as hydrobromic acid to cause decarboxylation reaction for removing the carboxyl group. Subsequently, the benzyl group can be removed, for example, by reacted with boron trifluoride etherate and dimethyl sulfide in a solvent such as methylene chloride.

In addition, the Compound (4), after converting its alkoxycarbonyl group to a carboxyl group as described in the above, can also be subjected to simultaneous removal of the carboxyl and benzyl groups by reacting with a strong acid such as hydrobromic acid. By employing hydrobromic acid, the reaction can be finished in a shortened period of time and in increased yields.

Furthermore, the Compound (4) can also be reacted, for example, with 47% hydrobromic acid to achieve improved yields by a progress of simultaneous removal of the alkoxycarbonyl and benzyl groups.

4-Hydroxypyrazolo[1,5-a]pyridine (5) as obtained by the form of alkali metal salt, with glycidyl tosylate to give 3-(pyrazolo[1,-5—a]pyrid-4-yloxy)-1,2-epoxypropane (6). The reaction is preferably carried out in a solvent such as dimethylformamide under an atmosphere of argon gas.

Then, the Compound (6) is reacted with isopropylamine to produce 1-(isopropylamino)-3-(pyrazolo[1,-5—a]pyrid-4-yloxy)-2-propanol (A), with approximately quantitative yields being achieved.

In the step of producing the Compound (6) from the Compound (5), optically active Compound (6) can be synthesized by employing glycidyl tosylate obtained by the tosylation of optically active glycidol, and optically active product compound (A) can be obtained by reacting the optically active Compound (6) with isopropylamine.

The Compound (A), which exhibits anti-serotonergic activity, can be used as an agent for treating neurosis, such as an antidepressant, antimania agent, etc. and can be administered orally or in a form of subcutaneous or intravenous injection. Its daily dose for human adults is 1 to 100 mg, preferably 10 to 20 mg, in the case of oral administration, and 0.05 to 20 mg, preferably 0.1 to 10 mg, in the case of injection. The Compound (A), because of the chemical configuration of its basic skeleton, is easily degradable and consequently becomes shorter in half-life period within the body, suggesting that it can alleviate adverse effects caused by accumulation of the drug.

In the meantime, in contrast to Pindolol, the Compound (A) did not show the blocking activity of β-adrenoceptor.

BRIEF DESCRIPTION OF THE DRAWING

Reverting to the drawings, FIG. 1 and FIG. 2 are bar graphs representing the results of the test on anti-serotonergic activity as conducted in Experiment Example where A denotes the compound according to this invention, that is 1-(isopropylamino)-3-(pyrazolo[1,5—a]-pyrid-4-yloxy)-2-propanol.

Below given are the Experiment Example and Examples to illustrate this invention more particularly.

EXPERIMENT EXAMPLE

In accordance with the method as described in Japanese Journal of Pharmacology (Japan. J. Pharmacol.), 51, 421–424 (1989), the Compound (A) was tested for its anti-serotonergic activity.

Animals

Male DBA strain mice (supplied by Japan SLC) weighing 20 to 25 g (6-weeks aged) were maintained on a 12 hr light-dark cycle from 7:00 to 19:00 at 24°±1° C., while they were allowed free access to food and water. The experiment was performed from 13:00 to 17:00.

Drug Substance and Method of Administration

A solution of the Compound (A) in isotonic saline was administered to the animals intraperitoneally, with isotonic saline in the same volume being administered to the control. 15 minutes after intraperitoneal application, Tryptamine was given each animal into the tail vein at a dose of 25 mg/kg.

Observation of Behavior

After administration of Tryptamine, mice were housed individually in each transparent plastic cage to observe their behavior. Among the serotonin syndrome induced after administration of tryptamine, the head weaving and hindlimb abduction which clearly appeared were scored every minutes in accordance with the following criteria of assessment:

0 = no appearance of the behavior observed (absent),
1 = behavior sustained for a period of less than 20 sec (occasional),
2 = behavior sustained for a period of not less than 20 sec but less than 40 sec (frequent),
3 = behavior sustained for not less than 40 sec (continuous). Observation was effected until behavior disappeared, and the results were expressed as a total score obtained by summing up individual scores recorded every minute.

Statistical Analysis

The scores recorded for the head weaving and hindlimb abduction were evaluated by Mann-Whitney's U-test.

The results are shown in FIG. 1 and FIG. 2.

As may be evident from each of the figures, the Compound (A), when given the animals, clearly suppressed the head weaving and hindlimb abduction in contrast to the control.

Consequently, it is considered evident that the Compound (A) exhibits anti-serotonergic activity.

EXAMPLE 1

Production of 3-benzyloxypyridine (2)

To a suspension of 3-hydroxypyridine (24.7 g, 260 mmole) in distilled methylene chloride (260 ml) were added Adogen 464 (1.6 ml), 40% NaOH (130 ml), benzyl chloride (32 ml, 278 mmole), followed by stirring for 3 days at room temperature. The organic layer was separated from the reaction solution, and the aqueous layer was admixed with water and extracted with methylene chloride. The resulting extract was combined with the methylene chloride layer separated previously, and the combined solution was washed with saturated saline, dried over $K_2CO_3$ and freed of the solvent by distillation. The residue was purified on a column of silica gel (7734, n-hexane:ethyl acetate=20:1 to 5:1).

Yield of 8.6 g or 17.9%.

EXAMPLE 2

Production of N-amino-3-benzyloxypyridinium mesitylenesulfonate (3)

A solution of O-mesitylenesulfonylhydroxylamine (13.7 g, 44.6 mmole, purity of 70%) in methylene chloride (150 ml) was added dropwise to a solution of 3-benzyloxypyridine (8.25 g, 44.6 mmole) in methylene chloride (150 ml) under ice-cooling, with stirring. The reaction solution was returned to room temperature, stirred for 1 hours and concentrated to one-quarter of the original volume at 20° to 30° C., and ether was added to the concentrate, thereby white crystals were precipitated. This product was used in the next reaction, without being purified.

Yield of 14.9 g or 83.3%.

The product was recrystallized from a mixed solution of methanol and ethyl acetate to give white flaky crystals having a melting point of 105° to 108° C.

Elemental analysis, for $C_{21}H_{24}O_4N_2S$: Calcd.: C, 62.99; H, 6.04; N, 7.00. Found: C, 62.85; H, 6.03; N, 6.71.

EXAMPLE 3

Production of methyl 4-benzyloxy-pyrazolo[1,5−a]-pyridine-3-carboxylate (4')

Anhydrous $K_2CO_3$ (5.8 g, 42.0 mmole) was added to a solution of the N-amino salt (3) (14.0 g, 35.0 mmole) in DMF (350 ml), and the mixture was stirred at room temperature for 2 to 3 minutes until it turned blue from initial green. Then, methyl propiolate (4.4 ml, 52.5 mmole) was added dropwise to the mixture, followed by stirring for 25 hours. The insoluble matter was filtered off from the reaction mixture, and solvent was removed from the filtrate by distillation. The residue was admixed with methylene chloride, resulting insoluble matter was filtered off, and solvent was removed from the filtrate by distillation. The residue was purified on a column of silica gel (9385, n-hexane:ethyl acetate=5:1 to 2:1). Yield of 4.7 g or 47.6%.

In this experiment, the 6-benzyloxy isomer was also produced simultaneously. Yield of 2.1 g or 21.1%.

The compound 4' was recrystallized from methyl acetate-n-hexane mixed solution to give white crystals with a melting point of 80.5° to 81.5° C.

Elemental analysis, for $C_{18}H_{14}O_3N_2$: Calcd.: C, 68.07; H, 5.00; N, 9.92. Found: C, 67.99; H, 4.99; N, 9.81.

EXAMPLE 4

Production of 4-hydroxypyrazolo[1,5−a]pyridine (5)

A suspension of the methyl ester derivative (4') (113 mg, 0.40 mmole) in 47% HBr (2 ml) was refluxed for 10 minutes. The reaction mixture was freed of the solvent by distillation as far as possible, and the residue was made alkaline (pH 8) with $NaHCO_3$. The resulting slurry was admixed with ethanol, insoluble matter was filtered off therefrom, and the filtrate was freed of the solvent by distillation. The same procedure was repeated once again, ether was added to the resulting residue, insoluble matter was filtered off therefrom, and the filtrate was freed of the solvent by distillation. The residue was purified on a column of silica gel (7734, chloroform).

Yield of 45 mg or 83.3%

Elemental analysis, for $C_7H_8ON_2$: Calcd.: C, 62.68; H, 4.51; N, 20.89. Found: C, 62.35; H, 4.63; N, 21.06.

EXAMPLE 5

Production of 3-(pyrazolo[1,5−a]pyrid-4-yloxy)-1,2-epoxypropane (6)

NaH (containing 60% of oil, 270 mg, 4.5 mmole) was washed with anhydrous petroleum ether, and was admixed, under atmosphere of argon gas, with distilled DMF (15 ml) and 4-hydroxypyrazolo[1,5−a]pyridine (5) (402 mg, 3.0 mmole), followed by stirring for 30 min to give a light pink suspension. Subsequently, glycidyl tosylate (821 mg, 3.6 mmole) was added to the suspension, followed by stirring overnight under atmosphere of argon gas to obtain a red-yellow suspension. The reaction mixture was neutralized by adding about 10 ml of saturated aqueous $NH_4Cl$, followed by addition of water (20 ml) and extraction with ether. The extract was washed with water, dried and freed of the solvent by distillation, and the residue was purified on a column of silica gel (7734, chloroform).

Yield of 350 mg or 61.4%.

NMR (CDCl$_3$)δ: 2.80 (dd, J=5.3 Hz, Hb), 2.95 (dd, J=5.4 Hz, Ha), 3.4–3.5 (m, Hc), 4.08 (dd, J=11.6 Hz, one of CH$_2$), 4.38 (dd, J=11.3 Hz, one of CH$_2$), 6.38 (d, J=7 Hz, H-5), 6.64 (t, J=7 Hz, H-6), 6.66 (dd, J=2.5, 1 Hz, H-3), 7.88 (d, J=2.5 Hz, H-2), 8.15 (d, J=7 Hz, H-7).

EXAMPLE 6

Production of 1-(isopropylamino)-3-(pyrazolo[1,5—a]pyrid-4-yloxy)-2-propanol (A)

The epoxy derivative (6) (336 mg, 1.77 mmole) was refluxed in isopropylamine-water (10:1) mixed solution for 45 minutes. The reaction solution was freed of the solvent by distillation, and the residue was admixed with chloroform. The mixture was dried, and the solvent was distilled off to give crystals showing one spot on TLC.

Yield of 431 mg or 98.0%.

The product was recrystallized from n-hexane to produce white crystals with a melting point of 65° to 67° C.

Elemental analysis, for C$_{13}$H$_{19}$O$_2$N$_3$: Calcd.: C, 62.62; H, 7.68; N, 16.85. Found: C, 62.76; H, 7.58; N, 16.73.

NMR (CDCl$_3$)δ 1.11 (d, J=6 Hz, CH$_3$x2), 2.0–2.3 (brs, NH and OH), 2.7–3.0 (m, —CH(OH)CH$_2$NH-CH—), 4.0–4.2 (m, —OCH$_2$CH(OH)—), 6.39 (brd, J=7 Hz, H-5), 6.62 (dd, J=2.5, 1 Hz, H-3), 6.64 (t, J=7 Hz, H-6), 7.87 (d, J=2.5 Hz, H-2), 8.15 (dt, J=7.1 Hz, H-7).

We claim:

1. A pyrazolo [1,5—a]pyridine compound represented by the formula:

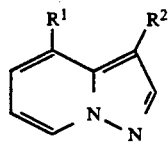

wherein
R$^1$ represents —OH, —OCH$_2$—phenyl,

—O—CH$_2$—CH—CH$_2$ (with epoxide O)

or —O—CH$_2$—CH(OH)—CH$_2$—NH—CH(CH$_3$)$_2$;

and R$^2$ is H, with the proviso that when R$^1$ is —OCH$_2$—phenyl, R$^2$ is COOR, wherein R is a C$_1$–C$_3$ alkyl group.

2. 1-(Isopropylamino)-3-(pyrazolo[1,5—a]pyrid-4-yloxy)-2-propanol of the formula:

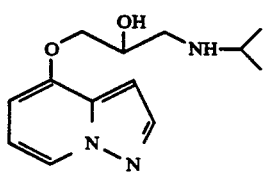

3. 3-(Pyrazolo[1,5—a]pyrid-4-yloxy)-1,2-epoxypropane of the formula:

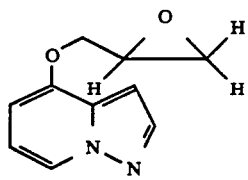

4. 4-Hydroxypyrazolo[1,5—a]pyridine of the formula:

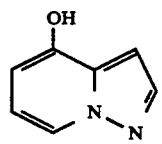

5. 4-Benzyloxy-pyrazolo[1,5—a]pyridine-3-carboxylic acid lower alkyl ester represented by the formula:

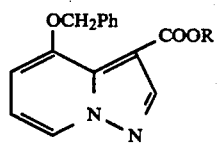

wherein Ph is a phenyl group and R represents a C$_1$–C$_3$ alkyl group.

6. A process for producing 1-(isopropylamino)-3-(pyrazolo[1,5—a]pyrid-4-yloxy)-2-propanol of the formula:

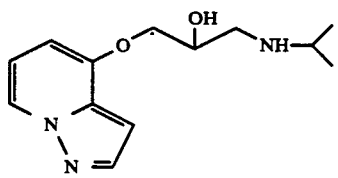

which process comprises reacting 3-(pyrazolo[1,5—a]-pyrid-4-yloxy)-1,2-epoxypropane of the formula:

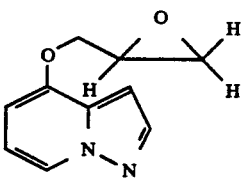

with isopropylamine.

7. A process for producing 1-(isopropylamino)-3-(pyrazolo[1,5—a]pyrid-4-yloxy)-2-propanol of the formula:

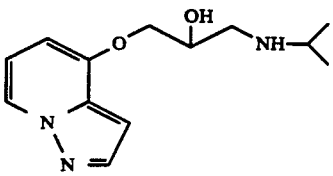

which process comprises reacting 3 benzyloxypridine obtained by O-benzylation of 3-hydroxypyridine with O-mesitylenesulfonylhydroxylamine to form N-amino-3-benzyloxypyridinium mesitylenesulfonate represented by the formula:

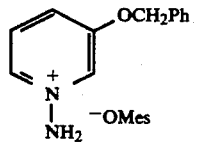

wherein Ph represents a phenyl group; and Mes represents a mesitylenesulfonic acid group, reacting the formed compound with a $C_1$–$C_3$ alkyl ester of propiolic acid to convert to a 4-benzyloxypyrazolo [1,5—a]pyridine-3-carboxylic acid lower alkyl ester represented by the formula:

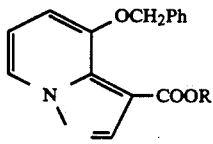

wherein Ph is the same as defined above; and R represents a $C_1$–$C_3$ alkyl group, subjecting the resulting compound to a reaction of removing the alkoxycarbonyl and benzyl groups to yield 4-hydroxypyrazolo[1,5—a]pyridine of the formula:

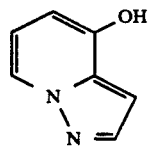

reacting the resultant compound with glycidyltosylate to produce 3-(pyrazolo[1,5—a]pyrid-4-yloxy)-1,2-epoxypropane of the formula:

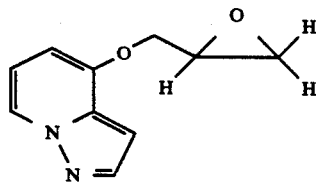

and reacting the resulting epoxypropane with isopropylamine to produce said 1-(isopropylamino)-3-(pyrazolo[1,5—a]pyrid-4-yloxy)-2-propanol.

8. A pharmaceutical composition which comprises 1-(isopropylamino)-3-(pyrazolo[1,5—a]pyrid-4-yloxy)-2-propanol of the formula:

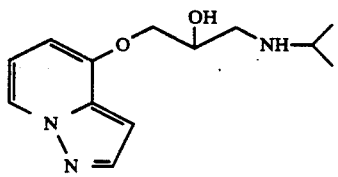

and a pharmaceutically acceptable carrier.

* * * * *

UNITED STATES PATENT AND TRADEMARK OFFICE
CERTIFICATE OF CORRECTION

PATENT NO. : 5,202,334
DATED : April 13, 1993
INVENTOR(S) : Takemura et al.

It is certified that error appears in the above-indentified patent and that said Letters Patent is hereby corrected as shown below:

Col. 9, line 1: delete "3 benzyloxypridine" and insert --3-benzyloxypyridine--

Col. 9, lines 25-30: delete the formula and insert the following:

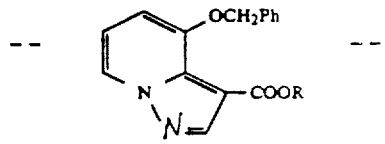

Signed and Sealed this

Eighth Day of March, 1994

Attest:

BRUCE LEHMAN

Attesting Officer          Commissioner of Patents and Trademarks